United States Patent
Taden et al.

(10) Patent No.: US 10,065,991 B2
(45) Date of Patent: Sep. 4, 2018

(54) PEPTIDES THAT CAN BE USED IN COATING AGENTS, ADHESION PROMOTERS OR ADHESIVES FOR OXIDIC SURFACES

(71) Applicant: HENKEL AG & CO. KGAA, Duesseldorf (DE)

(72) Inventors: Andreas Taden, Duesseldorf (DE); Birgit Veith, Duesseldorf (DE); Roland Breves, Mettmann (DE); Irmgard Schmidt, Solingen (DE); Thomas Weber, Dormagen (DE); Joachim Jose, Duesseldorf (DE); Claudia Reicheneder, Eschweiler (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 451 days.

(21) Appl. No.: 14/705,682

(22) Filed: May 6, 2015

(65) Prior Publication Data
US 2015/0259383 A1    Sep. 17, 2015

Related U.S. Application Data

(63) Continuation of application No. PCT/EP2013/073109, filed on Nov. 6, 2013.

(30) Foreign Application Priority Data

Nov. 7, 2012 (DE) .................. 10 2012 110 664

(51) Int. Cl.
*C07K 7/08* (2006.01)
*G01N 33/84* (2006.01)
*G01N 33/68* (2006.01)

(52) U.S. Cl.
CPC ........... *C07K 7/08* (2013.01); *G01N 33/6839* (2013.01); *G01N 33/84* (2013.01); *Y10T 428/31768* (2015.04)

(58) Field of Classification Search
CPC ...... C07K 7/08; G01N 33/84; G01N 33/6839; G01N 33/68; Y10T 428/31768
USPC ......... 428/478.2; 435/252.3, 252.31, 252.33, 435/254.11, 254.2, 254.21, 320.1; 436/501; 530/327; 536/23.1
See application file for complete search history.

(56) References Cited

U.S. PATENT DOCUMENTS

| | | | | |
|---|---|---|---|---|
| 4,239,495 A | | 12/1980 | Gindler et al. | |
| 4,554,254 A | | 11/1985 | Krystal | |
| 5,604,116 A | * | 2/1997 | Bauer | C07K 14/5403 424/85.2 |
| 5,677,149 A | * | 10/1997 | Bauer | C07K 14/5403 424/85.2 |
| 2007/0118916 A1 | * | 5/2007 | Puzio | C12N 15/8214 800/278 |
| 2011/0209241 A1 | * | 8/2011 | Hatzfeld | C12N 15/8261 800/278 |
| 2012/0164205 A1 | * | 6/2012 | Baum | A01N 63/02 424/409 |
| 2013/0035245 A1 | * | 2/2013 | Vreuls | C07K 7/08 506/9 |
| 2014/0199313 A1 | * | 7/2014 | Plesch | C12N 15/8214 424/139.1 |
| 2014/0259212 A1 | * | 9/2014 | Plesch | C12N 15/8243 800/278 |
| 2014/0325709 A1 | * | 10/2014 | Plesch | C07K 14/245 800/298 |

FOREIGN PATENT DOCUMENTS

| | | |
|---|---|---|
| CN | 1877289 | 12/2006 |
| CN | 101144823 | 3/2008 |
| CN | 101225604 | 7/2008 |
| CN | 101235229 A | 8/2008 |
| CN | 101392018 | 3/2009 |
| CN | 101865926 | 10/2010 |
| CN | 102680463 | 9/2012 |
| DE | 102005015043 | 10/2006 |
| JP | 2006225294 | 8/2006 |
| WO | 2003078451 | 9/2003 |
| WO | 2004035612 A2 | 4/2004 |
| WO | 2009018964 A2 | 2/2009 |
| WO | 2009065573 A1 | 5/2009 |
| WO | 2009079053 A2 | 6/2009 |
| WO | 2010000493 A2 | 1/2010 |

OTHER PUBLICATIONS

Lexikon der Biochemie, Spektrum Akademischer Verlag, Berlin, 1999, Band 1, S. 267-271 und Band 2, S. 227-229.
Rongjun Zuo et al., Aluminium- and mild steel-binding peptides from phage display, Appl Microbiol Biotechnol (2005) 64; 505-509.
Jose J., et al., Monitoring the cellular surface display of recombinant proteins by cysteine labeling and flow cytometry, Chembiochem (2003), 4(5), 396-405.
Jose J., et al., Cystope tagging for labeling and detection of recombinant protein expression Analytical Biochemistry (2004), 331(2), 267-274.

* cited by examiner

*Primary Examiner* — Douglas J McGinty
(74) *Attorney, Agent, or Firm* — Steven C. Bauman

(57) ABSTRACT

The present invention relates to peptides, in particular dodecapeptide-containing coating agents, adhesion promoters or adhesives for oxidic surfaces, a multilayer composite or a coated substrate, containing compounds which are formed entirely or in part of dodecapeptides as adhesion promoters between at least two adjacent layers of the composite or between the coating and the substrate, and to dodecapeptides that can be used as coating agents, adhesion promoters or adhesives for oxidic surfaces.

10 Claims, 1 Drawing Sheet
Specification includes a Sequence Listing.

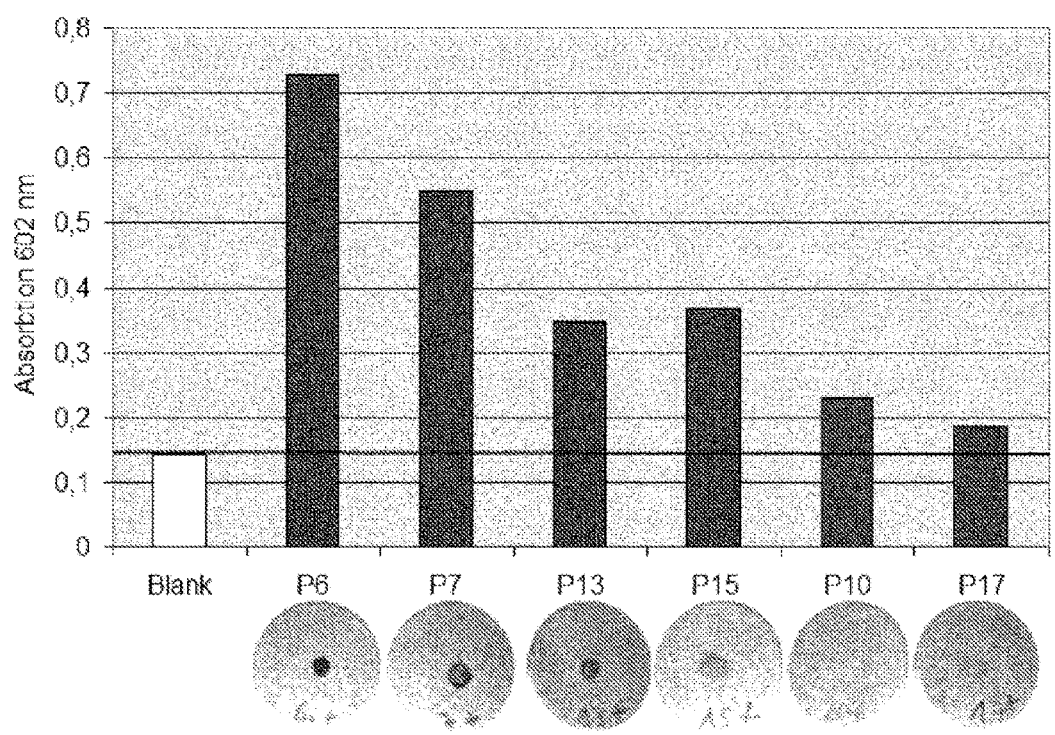

SEQUENCE LISTING

<160> NUMBER OF SEQ ID NOS: 19

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Nucleic acid encoding for peptide 6

<400> SEQUENCE: 1
tccagggcac gactatttgt agtcacatat cacaaa        36

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Nucleic acid encoding for peptide 7

<400> SEQUENCE: 2
cacatgatat ctacaatgaa cgcggcgagc cggcga        36

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Nucleic acid encoding for peptide 8

<400> SEQUENCE: 3
agaagcatag taacctttag tttaagacaa aatcgc        36

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Nucleic acid encoding for peptide 9

<400> SEQUENCE: 4
caacgtaatt tgattaaatc gacgtgccgg aaaatc        36

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Nucleic acid encoding for peptide 10

<400> SEQUENCE: 5
cgccagctcc agaggctgat gaaatcagta aattcg        36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Nucleic acid encoding for peptide 13

<400> SEQUENCE: 6
cgcaacacta ttcgtatacg gactataaaa catccg        36

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Nucleic acid encoding for peptide 15

<400> SEQUENCE: 7
cgacacagta gtactctgag gtataggcca cttccg        36

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Nucleic acid encoding for peptide 17

<400> SEQUENCE: 8
caacaaagtc gtcatatact gaatagaaaa aaaccg        36

<210> SEQ ID NO 9

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide 6

<400> SEQUENCE: 9

Ser Arg Ala Arg Leu Phe Val Val Thr Tyr His Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide 7

<400> SEQUENCE: 10

His Met Ile Ser Thr Met Asn Ala Ala Ser Arg Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide 8

<400> SEQUENCE: 11

Arg Ser Ile Val Thr Phe Ser Leu Arg Gln Asn Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide 9

<400> SEQUENCE: 12

Gln Arg Asn Leu Ile Lys Ser Thr Cys Arg Lys Ile
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide 10

<400> SEQUENCE: 13

Arg Gln Leu Gln Arg Leu Met Lys Ser Val Asn Ser
1               5                   10
```

```
<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide 13

<400> SEQUENCE: 14

Arg Asn Thr Ile Arg Ile Arg Thr Ile Lys His Pro
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide 15

<400> SEQUENCE: 15

Arg His Ser Ser Thr Leu Arg Tyr Arg Pro Leu Pro
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide 17

<400> SEQUENCE: 16

Gln Gln Ser Arg His Ile Leu Asn Arg Lys Lys Pro
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<223> OTHER INFORMATION: Peptide K1

<400> SEQUENCE: 17

Xaa Lys Arg Arg Pro Gly Xaa Xaa Val Glu Xaa Xaa
1               5                   10

<210> SEQ ID NO 18
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid
<220> FEATURE:
<223> OTHER INFORMATION: Peptide K2

<400> SEQUENCE: 18

His Asn Thr Ile Arg Ile Leu Thr Ile Lys Leu Xaa
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide K3

<400> SEQUENCE: 19

Arg His Ser Ser Thr Leu Arg Tyr Arg Pro His Pro
1               5                   10
```

PEPTIDES THAT CAN BE USED IN COATING AGENTS, ADHESION PROMOTERS OR ADHESIVES FOR OXIDIC SURFACES

CROSS REFERENCE TO RELATED APPLICATIONS

This application is a continuation of International Application No. PCT/EP2013/073109, filed Nov. 6, 2013, which claims the benefit of DE 102012110664.9, filed Nov. 7, 2012, the entireties of which are incorporated herein by reference.

SEQUENCE LISTING

The instant application contains a Sequence Listing which has been submitted electronically in ASCII format and is hereby incorporated by reference in its entirety. Said ASCII copy, created on May 28, 2015, is named 104388.000263_SL.txt and is 6,150 bytes in size.

FIELD OF THE DISCLOSURE

The invention relates to coating agents, adhesion promoters, or adhesives for oxidic surfaces, containing peptides, in particular dodecapeptides, to a multilayer composite or a coated substrate containing compounds that are completely or partially composed of dodecapeptides, as adhesion promoters between at least two adjoining layers of the composite or between the coating and the substrate, and to dodecapeptides that are usable as coating agents, adhesion promoters, or adhesives for oxidic surfaces.

BACKGROUND OF THE DISCLOSURE

In the area of coating or painting of oxidic surfaces, known methods for promoting adhesion involve bifunctional organosilane compounds, for example, which establish a chemical bond between the polymer matrix of the paint and the inorganic substrate. One disadvantage, among others, of these adhesion promoters is that optimal adhesion is ensured only when hydroxide groups with which the silane can interact are present on the surface of the substrate. In many cases, a complicated pretreatment of the substrate is therefore necessary for silanization of surfaces. In addition, the manufacture of customized materials is very complicated, and furthermore, customized materials are not known for all substrates.

Self-assembled monolayers (SAMs, also referred to as self-organizing monolayers) have been investigated and described since 1940, but it was not until 1983 that efforts were begun to make technical use of this organization process.

In principle, self-assembled monolayers have two different active groups, between which a spacer, for example an aliphatic spacer, is present. One group thereof interacts with the surface, and the other end group acts with a specific property or connects to another functional compound. The SAMs form chemical bonds which resist attack by water, and which at the same time are able to prevent all electrochemical reactions at the interlayers. The self-organization of the monomolecular layers on a solid surface provides an efficient method for producing an interlayer having a defined composition, structure, and thickness. Selectively self-organizing adhesion promoters have the advantage that they ensure adhesion of the paint layers and adhesive layers to metallic surfaces for long service lives, which is necessary in the automotive area, for example, for further improvement of the corrosion protection. The self-organizing adhesion promoters also allow consistently good adhesion of a uniform paint layer on the composite materials, which are being increasingly used, and which have different surfaces, such as plastic-metal composite materials.

Self-organizing monolayers are used in semiconductor technology, for example, for surface stabilization and customized functionalization of electrodes. The permeability and the charge transfer rate are influenced, depending on the length of the alkyl chains used. The field of application of self-organizing monolayers is very broad. The technology of the self-organizing monolayer is used, among other things, in the electrochemical scanning tunneling microscope, in cell studies, in sensor systems, and in nanoelectronics. However, production of the SAMs described in the prior art is complicated and costly.

The coupling of an inorganic substrate to biological components for modifying the surface properties is known in biomimetics. Bacteriophages, selected from a phage library, which present short peptides have been used, for example, to precipitate and separate inorganic materials (WO 2003/078451). In addition, hybrid materials composed of an inorganic substrate and specific peptide ligands are used as a potential approach for changing the substrate surface. However, identifying the biological ligand (usually a peptide) which matches the substrate is time- and cost-intensive, and heretofore has precluded a specific application. The concept of a bifunctional ligand for binding two inorganic components is addressed in the prior art. Specifically, the binding of cells or biomolecules to a polymer substrate, in particular an oxidized chlorine-doped polypyrrole (PPyCl) or poly(lactate co-glycolate) (PLGA), by bacteriophages having bifunctional binding properties is described in WO 2004/035612, for example. The further binding to another substance, which like a coating material, for example, is not a biological binding partner of the phage used, is not further described; this binding would likewise have to take place selectively and would require an exact match of the ligand to the further binding component.

Therefore, there is a great need to provide novel compounds which are suitable for use on oxidic surfaces, and which avoid the stated disadvantages of the prior art.

It has surprisingly been found that certain dodecapeptides may advantageously be used as coating agents, adhesion promoters, or adhesives for oxidic surfaces.

BRIEF DESCRIPTION OF THE DRAWING

FIG. 1 depicts the absorption of peptides P6, P7, P13, P15, P10, and P17.

SUMMARY

A subject matter of the present invention, therefore, relates to a quantification method for determining the adhesion properties on oxidic surfaces of adhering peptides, in particular dodecapeptides, which is characterized in that
a) a peptide-containing solution is applied to a carrier having an oxidic surface and allowed to dry,
b) the unbound peptides are removed from the carrier by washing, and the carrier is allowed to dry,
c) the peptides adhered to the carrier are stained with a staining solution, the remaining staining solution is washed off, and the carrier is allowed to dry, d) the stained peptides adhered to the carrier are removed from the carrier using an extraction solution, and the supernatant containing the stained peptides undergoes a spectrophotometric measurement.

DETAILED DESCRIPTION OF THE DISCLOSURE

The staining in step c) of the method according to the invention preferably takes place either by simple non-specific staining of the peptides, for example using Coomassie staining solution, or by a chemical reaction, for example with ninhydrin, which results in specific binding.

Steps a) to d) of the quantification method according to the invention are particularly advantageously carried out as follows:

In step a), 2×10 µL of a peptide solution, having a concentration of 2 mg/mL, dissolved in 1×PBS, pH 7.4, from Gibco, are applied to a round HDG steel plate having a diameter of 2.3 cm, wherein the first 10 µL is dried for approximately 15 minutes, and the second 10 µL is subsequently dropped onto the same location and dried for 30 minutes, followed by drying at 30° C. in a HB-1000 hybridization oven from UVP Laboratory Products in the presence of 200 mL water.

In step b), the plates are placed in a crystallizing dish (diameter 19 cm) containing 1 liter of 1×PBS, pH 7.4 for washing, and slightly agitated at 60 rpm in a Certomat U platform shaker from B. Braun for 10 minutes at room temperature, and subsequently dried at 30° C.

In step c), the plates are transferred into a 6-well dish, and 150 µL Coomassie staining solution, containing 2 g Coomassie brilliant blue R-250, 0.5 g Coomassie brilliant blue G-250, 50 mL methanol, 425 mL ethanol, 100 mL glacial acetic acid, and distilled water ad 1000 mL, is pipetted onto the plate, and after 30 seconds, 6 mL of 1×PBS buffer, pH 7.4, is carefully added at the edge of the dish for rinsing off the staining solution, and the plates are transferred into 2×6 mL of 1×PBS, pH 7.4, to remove the remaining staining solution, after which the plates are briefly dried at 30° C.

In step d), 20 µL DMSO/$CH_3COOH$ extraction solution in a volume ratio of 9/1 is pipetted onto the stained spots, the extraction solution is allowed to act for 5 minutes at room temperature, the liquid is subsequently drawn out by pipetting up and down until the spot is completely removed from the plate, and the supernatant is transferred into a reaction vessel, after which 2 µL of the supernatant is measured in a Nanodrop 1000 spectrophotometer from PeqLab, selecting the UV VIS program at 602 nm, in order to determine the color intensity that correlates with the adhesion strength of the peptides on oxidic surfaces.

Examples of oxidic surfaces that are suitable according to the invention are steel, glass, quartz, metal oxides ($B_2O_3$, $Al_2O_3$, $SiO_2$, $Fe_xO_y$, for example), ceramics, phosphated iron, rock, brick, and concrete, steel being particularly preferred. Keratinic fibers and oxidic polymers or appropriately functionalized polymers may also form oxidic surfaces that are suitable according to the invention.

The quantification method according to the invention advantageously allows an objective determination of the adhesion strength of peptides on oxidic surfaces, in particular of dodecapeptides on steel surfaces.

A further subject matter of the present invention relates to peptides, in particular dodecapeptides, which in the measurement in step d) of the quantification method according to the invention have an absorption in the range of 0.25 to 1, preferably 0.4 to 1, more preferably 0.5 to 1, particularly preferably 0.6 to 1, and very particularly preferably 0.7 to 1.

By means of the quantification method according to the invention, dodecapeptides have been identified whose amino acid sequence corresponds to the sequence pattern shown in Table 1, in which "X" stands for any amino acid; these dodecapeptides represent a further subject matter of the present invention.

Dodecapeptides which are preferred according to the invention are those which meet the sequence pattern shown in Table 1 at at least 8 of the 12 positions. Particularly preferred dodecapeptides are those which meet the sequence pattern shown in Table 1 at at least 10 of the 12 positions.

Very particularly preferred dodecapeptides according to the invention are peptides 8 and 9 listed in Table 1, and peptides 6 and 7 listed in Table 2.

A further subject matter of the present invention relates to peptides 10, 13, 15, and 17, in particular peptides 13 and 15, listed in Table 2.

A further subject matter of the present invention relates to nucleic acids which encode for the peptides according to the invention, in particular the nucleic acid sequences listed in Table 3.

In the sense of the present patent application, a peptide is understood to mean a polymer which is composed of the natural amino acids, has a largely linear structure, and is smaller than a natural protein. In the present patent application, the 19 proteinogenic, naturally occurring L-amino acids are designated by the internationally used 1- and 3-letter codes.

The peptides according to the invention, in particular dodecapeptides, may be chemically produced using known methods of peptide synthesis, for example by solid phase synthesis according to Merrifield.

However, it is preferred to produce the peptides according to the invention, in particular dodecapeptides, using recombinant methods. According to the invention, these are understood to mean all gene technology or microbiological methods which are based on introducing the genes for the peptides of interest into a host organism that is suitable for the production, and the host organism transcribing and translating the genes. The genes in question are suitably introduced via vectors, in particular expression vectors, but also via those vectors which act to allow the gene of interest in the host organism to be inserted into a genetic element that is already present, such as the chromosome, or other vectors. The functional unit composed of a gene and a promoter and possibly other genetic elements is referred to according to the invention as an "expression cassette." However, for this purpose the expression cassette does not necessarily also have to be present as a physical unit.

The peptides according to the invention, in particular dodecapeptides, are particularly preferably produced as multimers and subsequently cleaved into the functional peptides. Very particularly preferred multimers have 2 to 10 dodecapeptides, which in each case are separated from one another by spacers having a length of 0 to 4 amino acids. These spacers may be made up of the amino acids Gly, Ala, and Ser, for example.

Using methods which are currently generally known, such as chemical synthesis or the polymerase chain reaction (PCR), in conjunction with molecular biological and/or protein chemical standard methods, it is possible for those skilled in the art, on the basis of known DNA and/or amino acid sequences, to produce the corresponding nucleic acids and even complete genes. Such methods are known, for example, from Lexikon der Biochemie, [Lexicon of Biochemistry], Spektrum Akademischer Verlag, Berlin, 1999, Volume 1, pp. 267-271 and Volume 2, pp. 227-229.

The present invention also encompasses derivatives of the peptides according to the invention, in particular dodecapeptides. In the sense of the present patent application, derivatives are understood to mean those peptides whose pure amino acid chain has been chemically modified. Such derivatizations may, for example, take place biologically in conjunction with the biosynthesis by the host organism. Molecular biological methods may be used for this purpose. However, the derivatizations may also be carried out chemically, for example by the chemical conversion of a side chain of an amino acid or by covalent bonding of another compound to the peptide. Such a compound may also be, for example, other peptides or proteins which are bound to peptides according to the invention via bifunctional chemical compounds, for example. Derivatization is likewise understood to mean covalent bonding to a macromolecular carrier.

In the sense of the present invention, vectors are understood to mean elements which are composed of nucleic acids and which contain a gene of interest as a characterizing nucleic acid range. Vectors allow establishment of this gene in a species or a cell line over multiple generations or cell cleavages as a stable genetic element that is replicating itself independently of the rest of the genome. Vectors are specialized plasmids, i.e., circular genetic elements, in particular for use in bacteria. In genetic technology, a distinction is made on the one hand between those vectors which are used for storage, and thus, in a manner of speaking, also for the genetic work, the so-called cloning vectors, and on the other hand, those vectors which meet the function of implementing the gene of interest in the host cell, i.e., which enable the expression of the peptide in question. These vectors are referred to as expression vectors.

The nucleic acid which encodes for a peptide according to the invention, in particular a dodecapeptide, or a multimer of such a peptide, is suitably cloned into a vector. The molecular biological dimension of the invention, therefore, lies in vectors having the genes for the corresponding peptides. These may include vectors, for example, which are derived from bacterial plasmids, from viruses, or from bacteriophages, or predominantly synthetic vectors or plasmids with elements of various origins. With the further genetic elements which are present in each case, vectors are able to become established as stabile units in the host cells in question over several generations. In the sense of the invention, it is immaterial whether the vectors are established extrachomosomally as independent units, or are integrated into a chromosome. Which of the numerous systems known from the prior art is selected depends on the individual case. For example, the achievable copy number, the available selection systems, among them primarily antibiotic resistance, or the culturability of the host cells that are capable of accepting the vectors may be deciding factors.

The vectors form suitable starting points for molecular biological and biochemical investigations of the gene in question or the associated peptide, for developments according to the invention, and lastly, for amplifying and producing peptides according to the invention. The vectors represent further embodiments of the present invention.

Cloning vectors are preferred embodiments of the present invention. In addition to storage, they are suitable for biological amplification or selection of the gene of interest for characterization of the gene in question, for example via the creation of a restriction map or via sequencing. Cloning vectors are therefore also preferred embodiments of the present invention, since they represent a transportable and storable form of the claimed DNA. They are also preferred starting points for molecular biological techniques that are not tied to cells, for example the polymerase chain reaction.

Expression vectors are chemically similar to the cloning vectors, but differ in those partial sequences which enable the expression vectors to replicate in the host organisms which are optimized for the production of peptides and to express the gene contained therein. Expression vectors, which themselves bear the genetic elements necessary for expression, are preferred embodiments. The expression is influenced, for example, by promoters which regulate the transcription of the gene. Thus, the expression may take place due to the natural promoter which is originally localized in front of this gene, but also after genetic fusion, by a promoter of the host cell provided on the expression vector or also by a modified or completely different promoter of another organism.

Expression vectors which are regulatable via changes in the culture conditions, such as the cell density or specific factors, or by adding certain compounds, are preferred embodiments.

Embodiments of the present invention may also be cell-free expression systems in which the peptide biosynthesis is tracked in vitro. Such expression systems are likewise established in the prior art.

The in vivo synthesis of a peptide according to the invention, i.e., by living cells, requires transfer of the associated gene into a host cell, the so-called transformation thereof. In principle, all organisms, i.e., prokaryotes, eukaryotes, or Cyanophyta, are suitable as host cells. Host cells are preferred which may be easily managed genetically, which concerns, for example, transformation with the expression vector and stable establishment thereof, for example unicellular fungi or bacteria. In addition, preferred host cells are characterized by good microbiological and biotechnological manageability. This concerns, for example, ease of culturing, high growth rates, low demands on fermentation media, and good production and secretion rates for foreign peptides. It is often necessary to experimentally determine the optimal expression systems for the individual case from the large number of different systems that are available according to the prior art. Each peptide according to the invention may be obtained in this way from a variety of host organisms.

Those host cells whose activity is regulatable due to genetic regulation elements, which are provided on the expression vector, for example, but which may also be present in these cells from the outset, represent preferred embodiments. These host cells may be induced to express, for example by the controlled addition of chemical compounds which are used as activators, by changing the culturing conditions, or upon reaching a certain cell density. This allows very cost-effective production of the peptides of interest.

Prokaryotic or bacterial cells are preferred host cells. Bacteria, compared to eukaryotes, are generally characterized by shorter generation times and lower demands on the culturing conditions. Inexpensive methods for obtaining peptides according to the invention may thus be established. In the case of gram-negative bacteria, such as E. coli, numerous peptides are secreted into the periplasmatic space, i.e., the compartment between the two membranes which enclose the cells. This may be advantageous for particular applications. In contrast, gram-positive bacteria, for example Bacilli or Actinomycetes or other representatives of the Actinomycetales, have no outer membrane, so that secreted peptides are immediately delivered into the culture medium surrounding the cells, from which, according to another preferred embodiment, the expressed peptides according to the invention may be directly purified.

Expression systems in which additional genes, for example those which are provided on other vectors which influence the production of peptides according to the invention, represent a variant of this test principle. These may be modified gene products, or gene products which are to be purified together with the peptide according to the invention.

On account of the extensive experience with, for example, molecular biological methods and the culturability with coliform bacteria, these represent preferred embodiments of the present invention. Suitable strains for biotechnological production are particularly preferably those of the *Escherichia coli* species, in particular nonpathogenic bacteria.

Appropriate representatives of these species are the K12 derivatives and the B strains of *Escherichia coli*. Strains which may be derived therefrom according to genetic and/or microbiological methods that are known per se, and which therefore may be regarded as derivatives thereof, have the greatest importance for genetic and microbiological studies, and are preferably used for developing methods according to the invention. Such derivatives may be altered with regard to their requirements for the culture conditions, for example via deletion or insertion mutagenesis, may have different or additional selection markers, or may express different or additional peptides. These may in particular be those derivatives which, in addition to the peptide produced according to the invention, express further peptides of economic interest.

In addition, microorganisms are preferred which are characterized in that they have been obtained after transformation with one of the above-described vectors. These may be, for example, cloning vectors that have been introduced for storage and/or modification in an arbitrary bacterial strain. Such steps are fairly widespread in the storage and development of genetic elements in question. Since the genetic elements in question may be directly transferred from these microorganisms into gram-negative bacteria which are suitable for expression, the above-described transformation products are implementations of the applicable subject matter of the invention.

Eukaryotic cells may also be suitable for producing peptides according to the invention. Examples of such are fungi such as Actinomycetes or yeasts such as *Saccharomyces* or *Kluyveromyces*. This may be particularly advantageous, for example, when the peptides with regard to their synthesis are to undergo specific modifications which allow such systems. This includes, for example, the binding of low-molecular compounds such as membrane anchors or oligosaccharides.

The host cells of the method according to the invention are cultured and fermented in a manner known per se, for example in batch or continuous systems. In the first case, a suitable culture medium is inoculated with the recombinant bacterial strains, and the product is harvested from the medium after a period of time that is to be experimentally determined. Continuous fermentation is characterized by the achievement of a steady state in which, over a comparatively long time period, cells die in part, but are also replenished by growth, and at the same time, product may be withdrawn from the medium.

Fermentation methods are well known per se from the prior art, and represent the actual large-scale production step, followed by a suitable purification method.

All fermentation methods which are based on one of the above-mentioned methods for producing recombinant peptides represent correspondingly preferred embodiments of this subject matter of the invention.

In this regard, the conditions that are optimal in each case for the production methods used, for the host cells and/or the peptides to be produced, must be experimentally determined according to the knowledge of those skilled in the art, based on the previously optimized culture conditions of the strains in question, for example with regard to fermentation volume, media composition, oxygen supply, or agitator speed.

Fermentation methods which are characterized in that the fermentation is carried out via an inflow strategy are likewise suitable. In this regard, the media components that are consumed by the continuous culturing are replenished by feeding, also referred to as a feed strategy. Significant increases both in the cell density and in the dry biomass, and/or primarily in the activity of the peptide of interest, may be achieved in this way.

Analogously, the fermentation may also be designed in such a way that undesirable metabolic products are filtered out, or neutralized by adding a buffer, or counterions which are appropriate in each case.

The produced peptide may be subsequently harvested from the fermentation medium. This fermentation method is preferred over product preparation from the dry mass, but requires the provision of suitable secretion markers and transport systems.

In the absence of secretion, it is necessary, among other things, to purify the peptide from the cell mass; various methods for this purpose are known, such as precipitation by ammonium sulfate or ethanol, for example, or chromatographic purification, to the point of homogeneity, if necessary. However, the majority of the described technical methods should manage satisfactorily with an enriched, stabilized preparation.

All of the elements already described above may be combined into a method in order to produce peptides according to the invention. Numerous possible combinations of method steps are conceivable for each peptide according to the invention. The optimal method must be experimentally determined for each specific individual case.

A further subject matter of the present invention relates to nucleic acids which encode for peptides according to the invention, in particular dodecapeptides, and to cloning vectors and expression vectors which contain nucleic acids which encode for peptides according to the invention, in particular dodecapeptides.

The subject matter of the present invention further relates to prokaryotic or eukaryotic cells which have been transformed with nucleic acids which encode for peptides according to the invention, in particular dodecapeptides.

The peptides according to the invention, in particular dodecapeptides, may advantageously be used in coating agents, paints, and surface coatings, and adhesion promoters or adhesives for oxidic surfaces. The subject matter of the present invention therefore further relates to coating agents, paints, and surface coatings, and adhesion promoters or adhesives for oxidic surfaces, which contain the peptides according to the invention, in particular dodecapeptides, or which are composed of same.

A further subject matter of the present invention additionally relates to a multilayer composite or a coated substrate, containing compounds that are completely or partially composed of peptides, in particular dodecapeptides, as adhesion promoters between at least two adjoining layers of the composite or between the coating and the substrate.

Multilayer composites are used for various purposes, for example as packaging materials (in particular composite films) or self-adhesive articles (multilayer composite composed at least of one carrier and one adhesive layer). The multilayer composites according to the invention contain at least two, preferably two to five, layers, wherein the individual layers may have a thickness of 0.01 to 5 mm, for example.

The individual layers have oxidic surfaces, and preferably contain metal or metal oxides. The layers are in particular metal foils or metallized polymer films.

The above-mentioned peptides are used as adhesion promoters between at least two adjoining layers of the multilayer composite. At least one of the adjoining layers is preferably a layer made of a metallized natural or synthetic polymer. In particular polycondensates such as polyesters, polyadducts such as polyurethanes, polyamides, polycarbonates, or polyphenylene ethers, or polyphenylene sulfides, or polymers which are obtainable by radical or ionic polymerization of ethylenically unsaturated compounds (known as radical polymers for short) are suitable as polymers. These types of radical polymers are preferably composed of at least 60% by weight, particularly preferably at least 80% by weight, of so-called main monomers, selected from C1 to C20 alkyl(meth)acrylates, vinyl esters of carboxylic acids containing up to 20 C atoms, vinyl aromatics containing up to 20 C atoms, ethylenically unsaturated nitriles, vinyl halides, vinyl ethers of alcohols containing 1 to 10 C atoms, and aliphatic hydrocarbons containing 2 to 8 C atoms and one or two double bonds, in particular ethylene and propylene.

The quantity of the peptide necessary for adhesion promotion is generally 0.01 to 1000 milligrams per square meter ($mg/m^2$), in particular 0.01 to 100 $mg/m^2$ and particularly preferably 0.1 to 10 $mg/m^2$. The peptide according to the invention, in particular dodecapeptide, may be applied to one of the adjoining layers; alternatively, the peptide may be applied to both layers.

The peptide is preferably present as an aqueous solution; the peptide content of the solution is preferably 0.01 to 5 parts by weight peptide to 100 parts by weight water. For the uses according to the invention in coating agents, adhesion promoters, or adhesives for oxidic surfaces, the solution is preferably further diluted to a concentration of 1 to 10,000 µg/mL water, in particular 10 to 1000 µg/mL water.

After the application, drying may therefore initially take place to remove the water. The two adjoining layers may subsequently be joined by customary methods, such as lamination.

Substrates are coated for various purposes. Named in particular are decorative coatings or protective coatings (encompassing paints) or also adhesive coatings, wherein the adhesive as such may be applied to the substrate or adhesively affixed in the form of a self-adhesive article (label or adhesive tape), for example. The substrate or the substrate surface may be made of any material. Likewise, the coating or the substrate-side surface of the coating may be made of any material. The substrate surface or the coating, i.e., the substrate-side surface of the coating, is preferably made of metal, in particular steel, or of metallized natural or synthetic polymers.

In particular polycondensates such as polyesters, polyadducts such as polyurethanes, polyamides, polycarbonates, or polyphenylene ethers, or polyphenylene sulfides, or polymers which are obtainable by radical or ionic polymerization of ethylenically unsaturated compounds (known as radical polymers for short) are suitable as polymers. The above statements apply to the structure of the radical polymers and their content of main monomers.

The quantity of the peptide necessary for adhesion promotion corresponds to the quantity stated above. The peptide may be applied to the substrate surface, to the substrate-side surface of the coating, or to both. The peptide is preferably present as an aqueous solution; the content of the solution is as stated above. After the application, drying may therefore initially take place to remove the water.

The coating may be applied to the substrate according to customary methods, and films or multilayer composites may be laminated on, for example. In particular, the coating may be produced by applying a polymer dispersion, a polymer solution, or a solvent-free polymer to the substrate-side surface provided with the adhesion promoter, and subsequent filming and/or thermal or photochemical curing. For this purpose, the polymer is present in particular in the form of an aqueous dispersion or solution, and is particularly preferably an aqueous dispersion of an emulsion polymer, preferably one of the radical polymers stated above. After the polymer is applied, drying optionally takes place.

The multilayer composites and coated substrates according to the invention have greatly increased strength. Due to the use of the peptides as adhesion promoter, the coating adheres more strongly to the substrate, and the individual layers of the multilayer composite adhere to one another better.

In one very particularly preferred embodiment of the invention, the substrate is a metal. In principle, this may be any metal. Examples include iron, steel, zinc, tin, aluminum, copper, or alloys of these metals with one another and with other metals. The metal may in particular be steel, steel coated with zinc, zinc alloys, aluminum, or aluminum alloys, or may be aluminum or aluminum alloys. Zinc and zinc alloys, and thus substrates such as galvanized steel, for example, are particularly preferred.

Zn or Al alloys are known to those skilled in the art. Those skilled in the art will select the type and quantity of alloy components, depending on the desired application. Typical components of zinc alloys comprise in particular Al, Pb, Si, Mg, Sn, Cu, or Cd. Typical components of aluminum alloys comprise in particular Mg, Mn, Si, Zn, Cr, Zr, Cu, or Ti. These may also be Al/Zn alloys, in which Al and Zn are present in approximately equal quantities. Steel coated with alloys of this type is commercially available.

The metals may be present in any form, but preferably are metal foils, metal strips, or metal sheets. The metal may also be a composite material having a metallic surface. For example, the composite material may be a composite made of a polymer film and a metal.

The oxidic, preferably metallic, surfaces are coated with the peptides according to the invention as adhesion promoter. This may be carried out using aqueous solutions of the peptides. Particulars of the coating have already been mentioned above.

The coating may in particular be typical paints or paint systems for coating metallic surfaces. These paints or paint systems may be paints which cure thermally, photochemically, or by other mechanisms.

Typical paints for coating metal surfaces include at least one binder, and crosslinkable components. The crosslinkable components may be crosslinkers which are used in addition to a binder, or may be crosslinkable groups which are joined to the binder. Of course, the binder may also have crosslinkable groups, and in addition a crosslinker may be used. Various possible combinations are conceivable. For example, the binder and the crosslinker may be used separately. The binder then includes reactive functional groups which are able to react with complementary, reactive functional groups in the crosslinkers. Alternatively, the binders may be self-crosslinking binders which include reactive functional groups that are able to take part in crosslinking reactions with groups of their type ("with themselves") or with complementary, reactive functional groups on the same polymer. It is also possible that only the crosslinkers react with one another.

Examples of suitable binders include (meth)acrylate (co) polymers, partially saponified polyvinyl esters, polyesters, alkyd resins, polylactones, polycarbonates, polyethers, epoxy resin-amine addition products, polyureas, polyamides, polyimides, or polyurethanes. Of course, mixtures of various polymers may also be used, provided that no undesirable effects result from the mixture. The crosslinking components may have thermally crosslinking groups or photochemically crosslinking groups. Suitable thermal crosslinkers are, for example, crosslinkers based on epoxides, melamine, or blocked isocyanates. Suitable crosslinkers for photochemical crosslinking are in particular compounds containing multiple ethylenically unsaturated groups, in particular di- or polyfunctional acrylates.

The adhesion of paint to the substrate is advantageously improved by the peptides according to the invention, in particular dodecapeptides. In addition, improved resistance against infiltration of the paint layer is achieved in corrosion protection tests.

A further subject matter of the present invention therefore relates to the use of peptides according to the invention, in particular dodecapeptides, as a component of coating agents, paints, and surface coatings, of adhesion promoters or adhesives for oxidic surfaces, and of multilayer composites or coated substrates.

The following examples explain the invention, but without limiting the invention thereto:

EXAMPLE 1

Quantification of Peptides on (Steel) Surfaces

Using the method described below, it is illustrated how peptides adhered to (steel) surfaces may be quantified.

It is thus possible, apart from visual assessment, to produce an objectively measurable result with regard to the adhesion properties. This method is to be understood as an example; other chemical detection methods may be similarly suitable (for example, reaction with ninhydrin).

Using the described method, the peptides listed in Table 3 may be discriminated, and a distinction may be made between good (P6, P7), moderate (P13, P15), and poor to non-binding peptides (10, 17), as is apparent in the graphic shown in FIG. 1.

Application of the peptides:
2×10 µL peptide solution (2 mg/mL dissolved in 1×PBS, pH 7.4, from Gibco) was applied to a HDG steel plate (round, diameter 2.3 cm). The first 10 µL was dried for approximately 15', and the second 10 µL was subsequently dropped onto the same location and dried for 30'. Drying was carried out at 30° C. in a HB-1000 hybridization oven from UVP in the presence of 200 mL water.

Washing:
The plates were placed in a crystallizing dish (diameter 19 cm), containing 1 liter of 1×PBS, pH 7.4, for washing and slightly agitated at 60 rpm in a Certomat U apparatus from B. Braun for 10' at RT. The plates were subsequently dried at 30° C.

Staining:
The plates were transferred into a 6-well dish. 150 µL Coomassie staining solution was pipetted onto the plate. After 30 seconds, 6 mL of 1×PBS buffer, pH 7.4, was carefully added at the edge for rinsing off the staining solution. The plate was subsequently transferred into 2×6 mL of 1×PBS, pH 7.4, to remove the remaining staining solution. The plate was briefly dried at 30° C. (Coomassie staining solution: 2 g Coomassie brilliant blue R-250, 0.5 g Coomassie brilliant blue G-250, 50 mL methanol, 425 mL ethanol, 100 mL glacial acetic acid, and distilled water ad 1000 mL.)

Removal:
20 µL DMSO/$CH_3COOH$ solution (v/v 9/1) was pipetted onto the stained spot. The extraction solution was allowed to act for 5' at RT, and the liquid was subsequently drawn out by pipetting up and down until the spot was completely removed from the plate. The supernatant was transferred into a reaction vessel.

Measurement:
The measurement of the color intensity was performed in a Nanodrop 1000 spectrophotometer (UV VIS program). For this purpose, a 2-µL sample was applied and measured at 602 nm.

Tables:

TABLE 1

| Position: | 1 | 2 | 3 | 4 | 5 | 6 | 7 | 8 | 9 | 10 | 11 | 12 |
|---|---|---|---|---|---|---|---|---|---|---|---|---|
| Peptide K1 (SEQ ID NO: 17) | X | K | R | R | P | G | X | X | V | E | X | X |
| Peptide K2 (SEQ ID NO: 18) | H | N | T | I | R | I | L | T | I | K | L | X |
| Peptide K3 (SEQ ID NO: 19) | R | H | S | S | T | L | R | Y | R | P | H | P |
| Peptide 8 (SEQ ID NO: 11) | R | S | I | V | T | F | S | L | R | Q | N | R |
| Peptide 9 (SEQ ID NO: 12) | Q | R | N | L | I | K | S | T | C | R | K | I |

X: any amino acid

TABLE 2

| Peptide No. | AA sequence 1 2 3 4 5 6 7 8 9 10 11 12 | Adhesive assay HDG stainless steel Quantitative Coomassie evaluation (absorption: 602 nm) |
|---|---|---|
| 6 (SEQ ID NO: 9) | S R A R L F V V T Y H K | 0.728 |
| 7 (SEQ ID NO: 10) | H M I S T M N A A S R R | 0.549 |
| 13 (SEQ ID NO: 14) | R N T I R I R T I K H P | 0.348 |

TABLE 2-continued

| Peptide No. | AA sequence 1 2 3 4 5 6 7 8 9 10 11 12 | Adhesive assay HDG stainless steel Quantitative Coomassie evaluation (absorption: 602 nm) |
|---|---|---|
| 15 (SEQ ID NO: 15) | R H S S T L R Y R P L P | 0.369 |
| 10 (SEQ ID NO: 13) | R Q L Q R L M K S V N S | 0.229 |
| 17 (SEQ ID NO: 16) | Q Q S R H I L N R K K P | 0.186 |

TABLE 3

Nucleotide sequences which encode for peptides according to the invention

| Peptide | Sequence |
|---|---|
| Peptide 6 | tccagggcacgactatttgtagtcacatatcacaaa (SEQ ID NO: 1) |
| Peptide 7 | cacatgatatctacaatgaacgcggcgagccggcga (SEQ ID NO: 2) |
| Peptide 8 | agaagcatagtaacctttagtttaagacaaaatcgc (SEQ ID NO: 3) |
| Peptide 9 | caacgtaatttgattaaatcgacgtgccggaaaatc (SEQ ID NO: 4) |
| Peptide 10 | cgccagctccagaggctgatgaaatcagtaaattcg (SEQ ID NO: 5) |
| Peptide 13 | cgcaacactattcgtatacggactataaaacatccg (SEQ ID NO: 6) |
| Peptide 15 | cgacacagtagtactctgaggtataggccacttccg (SEQ ID NO: 7) |
| Peptide 17 | caacaaagtcgtcatatactgaatagaaaaaaaccg (SEQ ID NO: 8) |

The invention claimed is:

1. A coating agent, paint, surface coating, adhesion promoter, or adhesive for oxidic surfaces comprising a peptide, comprising a peptide with an amino acid sequence of any one of SEQ ID Nos: 9-19.

2. A multilayer composite or substrate having a coating, comprising a compound that is completely or partially composed of a peptide with an amino acid sequence of any one of SEQ ID Nos: 9-19 as an adhesion promoter between at least two adjoining layers of the composite or between the coating and the substrate.

3. The coating agent, paint, surface coating, adhesion promoter, or adhesive for oxidic surfaces of claim 1, comprising a peptide with an amino acid sequence of any one of SEQ ID Nos: 9-19, wherein the peptide binds to an oxidic surface.

4. The multilayer composite or coated substrate of claim 2 comprising the amino acid sequence of any one of SEQ ID Nos: 9-19, wherein the peptide binds to an oxidic surface.

5. The coating agent, paint, surface coating, adhesion promoter, or adhesive for oxidic surfaces of claim 1 comprising a nucleic acid that encodes for an amino acid sequence of any one of SEQ ID Nos: 9-19.

6. The multilayer composite or coated substrate of claim 2, comprising a nucleic acid that encodes for an amino acid sequence of any one of SEQ ID Nos: 9-19.

7. The coating agent, paint, surface coating, adhesion promoter, or adhesive for oxidic surfaces of claim 1, comprising a vector comprising a nucleic acid that encodes for an amino acid sequence of any one of SEQ ID Nos: 9-19.

8. The coating agent, paint, surface coating, adhesion promoter, or adhesive for oxidic surfaces of claim 1, comprising a vector comprising a nucleic acid that encodes for an amino acid sequence of any one of SEQ ID Nos: 9-19.

9. The coating agent, paint, surface coating, adhesion promoter, or adhesive for oxidic surfaces of claim 1, comprising a prokaryotic or eukaryotic cell that has been transformed with a nucleic acid that encodes for an amino acid sequence of any one of SEQ ID Nos: 9-19.

10. The coating agent, paint, surface coating, adhesion promoter, or adhesive for oxidic surfaces of claim 1, comprising a prokaryotic or eukaryotic cell that has been transformed with a nucleic acid that encodes for an amino acid sequence of any one of SEQ ID Nos: 9-19.

* * * * *